US011350885B2

(12) United States Patent
Vatanparvar et al.

(10) Patent No.: US 11,350,885 B2
(45) Date of Patent: Jun. 7, 2022

(54) SYSTEM AND METHOD FOR CONTINUOUS PRIVACY-PRESERVED AUDIO COLLECTION

(71) Applicant: Samsung Electronics Co., Ltd., Suwon-si (KR)

(72) Inventors: Korosh Vatanparvar, Santa Clara, CA (US); Viswam Nathan, Mountain View, CA (US); Ebrahim Nematihosseinabadi, Mountain View, CA (US); Md Mahbubur Rahman, San Jose, CA (US); Jilong Kuang, San Jose, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 171 days.

(21) Appl. No.: 16/784,032

(22) Filed: Feb. 6, 2020

(65) Prior Publication Data
US 2020/0258535 A1 Aug. 13, 2020

Related U.S. Application Data

(60) Provisional application No. 62/865,747, filed on Jun. 24, 2019, provisional application No. 62/803,112, filed on Feb. 8, 2019.

(51) Int. Cl.
*G10L 13/00* (2006.01)
*A61B 5/00* (2006.01)
(Continued)

(52) U.S. Cl.
CPC ............ *A61B 5/7267* (2013.01); *G10L 13/00* (2013.01); *G10L 15/02* (2013.01); *G10L 15/04* (2013.01); *G10L 15/22* (2013.01); *G10L 25/84* (2013.01)

(58) Field of Classification Search
CPC ............... A61B 5/7267; A61B 5/7203; A61B 2560/0242; A61B 5/4803; G10L 13/00;
(Continued)

(56) References Cited

U.S. PATENT DOCUMENTS 8,311,819 B2 * 11/2012 Hetherington .......... G10L 25/87
704/233
10,685,669 B1 * 6/2020 Lan ...................... G10L 15/1822
(Continued)

FOREIGN PATENT DOCUMENTS

WO 2011066844 A1 6/2011

OTHER PUBLICATIONS

Nguyen, K. A., & Luo, Z. (Jun. 2018). Cover your cough: Detection of respiratory events with confidence using a smartwatch. In Conformal and Probabilistic Prediction and Applications (pp. 114-131). PMLR (Year: 2018).*
(Continued)

*Primary Examiner* — Edgar X Guerra-Erazo
*Assistant Examiner* — Nandini Subramani

(57) ABSTRACT

A method includes identifying, by an electronic device, one or more segments within a first audio recording that includes one or more non-speech segments and one or more speech segments. The method also includes generating, by the electronic device, one or more synthetic speech segments that include natural speech audio characteristics and that preserve one or more non-private features of the one or more speech segments. The method also includes generating, by the electronic device, an obfuscated audio recording by replacing the one or more speech segments with the one or more synthetic speech segments while maintaining the one or more non-speech segments, wherein the one or more synthetic speech segments prevent recognition of some content of the obfuscated audio recording.

20 Claims, 10 Drawing Sheets

(51) Int. Cl.
*G10L 15/02* (2006.01)
*G10L 15/04* (2013.01)
*G10L 15/22* (2006.01)
*G10L 25/84* (2013.01)

(58) Field of Classification Search
CPC ......... G10L 15/02; G10L 15/04; G10L 15/22; G10L 25/84; G10L 25/66; G10L 25/87; G10L 25/78; H04K 1/02; H04K 1/04; G16H 50/20; G16H 40/67; G16H 40/63; H04W 12/02
See application file for complete search history.

(56) References Cited

U.S. PATENT DOCUMENTS

| | | | |
|---|---|---|---|
| 2004/0019479 A1* | 1/2004 | Hillis | H04K 1/06 704/200.1 |
| 2008/0037719 A1* | 2/2008 | Doren | G06F 21/6263 379/85 |
| 2008/0281220 A1 | 11/2008 | Sharifpour | |
| 2009/0306988 A1* | 12/2009 | Chen | H04K 1/04 704/261 |
| 2010/0305949 A1* | 12/2010 | Kato | G10L 13/06 704/266 |
| 2012/0053931 A1* | 3/2012 | Holzrichter | G10K 11/1754 704/200.1 |
| 2012/0059650 A1* | 3/2012 | Faure | G10L 21/0208 704/226 |
| 2012/0239406 A1* | 9/2012 | Langehoveen Brummer | G10L 21/00 704/264 |
| 2013/0163781 A1* | 6/2013 | Thyssen | G10L 25/51 381/94.3 |
| 2015/0126888 A1 | 5/2015 | Patel et al. | |
| 2018/0322961 A1* | 11/2018 | Kim | G16H 80/00 |
| 2019/0172458 A1* | 6/2019 | Mishra | G10L 15/063 |
| 2019/0269371 A1 | 9/2019 | O'keeffe et al. | |

OTHER PUBLICATIONS

Sun, X., Lu, Z., Hu, W., & Cao, G. (Sep. 2015). SymDetector: detecting sound-related respiratory symptoms using smartphones. In Proceedings of the 2015 ACM International Joint Conference on Pervasive and Ubiquitous Computing (pp. 97-108) (Year: 2015).*

Communication pursuant to Article 94(3) EPC in connection with European Application No. 20156065.3 dated Dec. 18, 2020, 6 pages.

Larson, et al., "Accurate and Privacy Preserving Cough Sensing using a Low-Cost Microphone," UbiComp '11 Proceedings of the 13th International Conference on Ubiquitous Computing, Sep. 2011, 10 pages.

European Search Report in connection with European Application No. 20156065.3 dated Apr. 1, 2020, 10 pages.

Chen, Francine, et al., "Audio Privacy: Reducing Speech Intelligibility while Preserving Environmental Sounds," ACM Multimedia, Proceedings of the International Conference (MM '08), Oct. 26, 2008, 4 pages.

Lee, Sujee, et al., "Configurable Pulmonary-Tuned Privacy Preservation Algorithm for Mobile Devices," 2018 IEEE International Conference on Bioinformatics and Biomedicine (BIBM), IEEE, Dec. 3, 2018, 6 pages.

Vatanparvar, Korosh, et al., "A Generative Model for Speech Segmentation and Obfuscation for Remote Health Monitoring," 2019 IEEE 16th International Conference on Wearable and Implantable Body Sensor Networks (BSN), May 19, 2019, 4 pages.

European Patent Office, "Communication under Rule 71(3) EPC" dated Sep. 10, 2021, in connection with European Patent Application No. 20156065.3, 53 pages.

* cited by examiner

SYSTEM AND METHOD FOR CONTINUOUS PRIVACY-PRESERVED AUDIO COLLECTION

CROSS-REFERENCE TO RELATED APPLICATIONS AND PRIORITY CLAIM

This application claims priority under 35 U.S.C. § 119(e) to U.S. Provisional Patent Application No. 62/803,112, filed on Feb. 8, 2019, and to U.S. Provisional Patent Application No. 62/865,747 filed on Jun. 24, 2019. Both of these applications are hereby incorporated by reference in their entirety.

TECHNICAL FIELD

This disclosure relates generally to health monitoring systems and methods. More specifically, this disclosure relates to a system and method for continuous, privacy-preserved collection of audio.

BACKGROUND

Recent technological advances in wearable devices and artificial intelligence (AI) are transforming health care by enabling proactive mobile health and ubiquitous monitoring of a health condition of a user/patient/subject outside of conventional clinical settings. However, a major arising issue is privacy and possible misuse of highly sensitive patient Protected Health Information (PHI) and data. Various entities may have significant interests in collecting subjects' private data and sharing them with marketing organizations, insurance companies, research institutions, government agencies, or the like.

SUMMARY

This disclosure provides a system and method for continuous, privacy-preserved collection of audio.

In a first embodiment, a method includes identifying, by an electronic device, one or more segments within a first audio recording that includes one or more non-speech segments and one or more speech segments. The method also includes generating, by the electronic device, one or more synthetic speech segments that include natural speech audio characteristics and that preserve one or more non-private features of the one or more speech segments. The method also includes generating, by the electronic device, an obfuscated audio recording by replacing the one or more speech segments with the one or more synthetic speech segments while maintaining the one or more non-speech segments, wherein the one or more synthetic speech segments prevent recognition of some content of the obfuscated audio recording.

In a second embodiment, an electronic device includes at least one audio sensor configured to generate a first audio recording. The electronic device also includes a processor configured to identify one or more segments within the first audio recording that includes one or more non-speech segments and one or more speech segments; generate one or more synthetic speech segments that include natural speech audio characteristics and that preserve one or more non-private features of the one or more speech segments; and generate an obfuscated audio recording by replacing the one or more speech segments with the one or more synthetic speech segments while maintaining the one or more non-speech segments, wherein the one or more synthetic speech segments prevent recognition of some content of the obfuscated audio recording.

In a third embodiment, a non-transitory computer readable medium contains computer readable program code that, when executed, causes at least one processor of an electronic device to identify one or more segments within a first audio recording that includes one or more non-speech segments and one or more speech segments; generate one or more synthetic speech segments that include natural speech audio characteristics and that preserve one or more non-private features of the one or more speech segments; and generate an obfuscated audio recording by replacing the one or more speech segments with the one or more synthetic speech segments while maintaining the one or more non-speech segments, wherein the one or more synthetic speech segments prevent recognition of some content of the obfuscated audio recording.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

As used here, terms and phrases such as "have," "may have," "include," or "may include" a feature (like a number, function, operation, or component such as a part) indicate the existence of the feature and do not exclude the existence of other features. Also, as used here, the phrases "A or B," "at least one of A and/or B," or "one or more of A and/or B" may include all possible combinations of A and B. For example, "A or B," "at least one of A and B," and "at least one of A or B" may indicate all of (1) including at least one A, (2) including at least one B, or (3) including at least one A and at least one B.

As used here, the terms "first" and "second" may modify various components regardless of importance and do not limit the components. These terms are only used to distinguish one component from another. For example, a first user device and a second user device may indicate different user devices from each other, regardless of the order or importance of the devices. A first component may be denoted a second component and vice versa without departing from the scope of this disclosure.

It will be understood that, when an element (such as a first element) is referred to as being (operatively or communicatively) "coupled with/to" or "connected with/to" another element (such as a second element), it can be coupled or connected with/to the other element directly or via a third element. In contrast, it will be understood that, when an element (such as a first element) is referred to as being "directly coupled with/to" or "directly connected with/to" another element (such as a second element), no other element (such as a third element) intervenes between the element and the other element.

As used here, the phrase "configured (or set) to" may be interchangeably used with the phrases "suitable for," "having the capacity to," "designed to," "adapted to," "made to," or "capable of" depending on the circumstances. The phrase "configured (or set) to" does not essentially mean "specifically designed in hardware to." Rather, the phrase "configured to" may mean that a device can perform an operation together with another device or parts. For example, the phrase "processor configured (or set) to perform A, B, and C" may mean a generic-purpose processor (such as a CPU or application processor) that may perform the operations by executing one or more software programs stored in a memory device or a dedicated processor (such as an embedded processor) for performing the operations.

The terms and phrases as used here are provided merely to describe some embodiments of this disclosure but not to limit the scope of other embodiments of this disclosure. It is to be understood that the singular forms "a," "an," and "the" include plural references unless the context clearly dictates otherwise. All terms and phrases, including technical and scientific terms and phrases, used here have the same meanings as commonly understood by one of ordinary skill in the art to which the embodiments of this disclosure belong. It will be further understood that terms and phrases, such as those defined in commonly-used dictionaries, should be interpreted as having a meaning that is consistent with their meaning in the context of the relevant art and will not be interpreted in an idealized or overly formal sense unless expressly so defined here. In some cases, the terms and phrases defined here may be interpreted to exclude embodiments of this disclosure.

Examples of an "electronic device" according to embodiments of this disclosure may include at least one of a smart phone, a tablet personal computer (PC), a mobile phone, a video phone, an e-book reader, a desktop PC, a laptop computer, a netbook computer, a workstation, a personal digital assistant (PDA), a portable multimedia player (PMP), an MP3 player, a mobile medical device, a camera, or a wearable device (such as smart glasses, a head-mounted device (HMD), electronic clothes, an electronic bracelet, an electronic necklace, an electronic appcessory, an electronic tattoo, a smart mirror, or a smart watch). Other examples of an electronic device include a smart home appliance. Examples of the smart home appliance may include at least one of a television, a digital video disc (DVD) player, an audio player, a refrigerator, an air conditioner, a cleaner, an oven, a microwave oven, a washer, a drier, an air cleaner, a set-top box, a home automation control panel, a security control panel, a TV box (such SAMSUNG HOMESYNC, APPLETV, or GOOGLE TV), a gaming console (such as an XBOX, PLAYSTATION, or NINTENDO), an electronic dictionary, an electronic key, a camcorder, or an electronic picture frame. Still other examples of an electronic device include at least one of various medical devices (such as diverse portable medical measuring devices (like a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global positioning system (GPS) receiver, an event data recorder (EDR), a flight data recorder (FDR), an automotive infotainment device, a sailing electronic device (such as a sailing navigation device or a gyro compass), avionics, security devices, vehicular head units, industrial or home robots, automatic teller machines (ATMs), point of sales (POS) devices, or Internet of Things (IoT) devices (such as a bulb, various sensors, electric or gas meter, sprinkler, fire alarm, thermostat, street light, toaster, fitness equipment, hot water tank, heater, or boiler). Other examples of an electronic device include at least one part of a piece of furniture or building/structure, an electronic board, an electronic signature receiving device, a projector, or various measurement devices (such as devices for measuring water, electricity, gas, or electromagnetic waves). Note that, according to embodiments of this disclosure, an electronic device may be one or a combination of the above-listed devices. According to some embodiments of this disclosure, the electronic device may be a flexible electronic device. The electronic device disclosed here is not limited to the above-listed devices and may include new electronic devices depending on the development of technology.

In the following description, electronic devices are described with reference to the accompanying drawings, according to embodiments of this disclosure. As used here, the term "user" may denote a human or another device (such as an artificial intelligent electronic device) using the electronic device.

Definitions for other certain words and phrases may be provided throughout this patent document. Those of ordinary skill in the art should understand that in many if not most instances, such definitions apply to prior as well as future uses of such defined words and phrases.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle. Use of any other term, including without limitation "mechanism," "module," "device," "unit," "component," "element," "member," "apparatus," "machine," "system," "processor," or "controller," within a claim is understood by the Applicant to refer to structures known to those skilled in the relevant art and is not intended to invoke 35 U.S.C. § 112(f).

BRIEF DESCRIPTION OF THE DRAWINGS

For a more complete understanding of this disclosure and its advantages, reference is now made to the following description, taken in conjunction with the accompanying drawings, in which.

DETAILED DESCRIPTION

Figure 1:
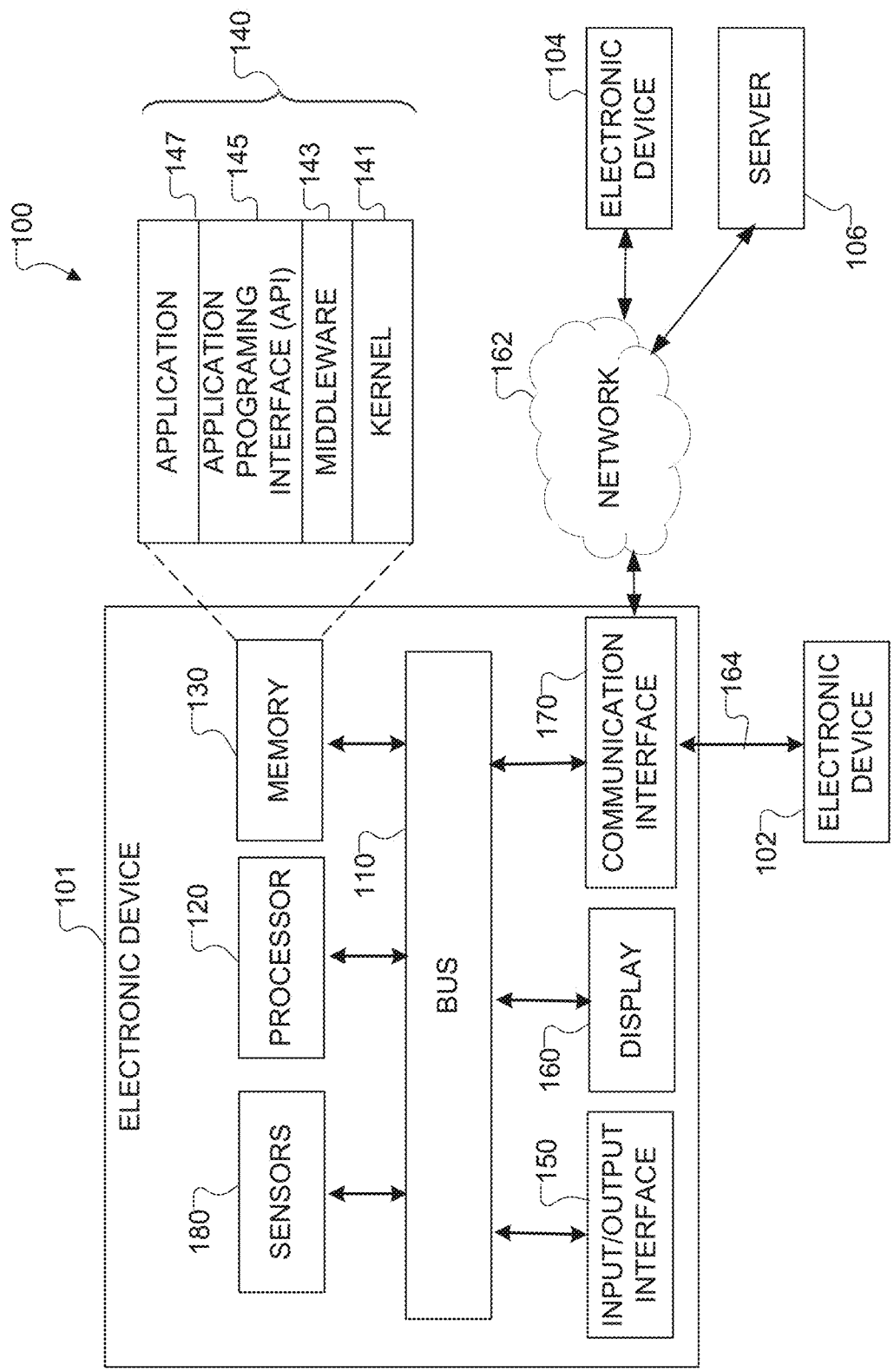
FIG. 1 illustrates an example network configuration in accordance with this disclosure.

The figures discussed below and the various embodiments used to describe the principles of this disclosure in this patent document are by way of illustration only and should not be construed in any way to limit the scope of the disclosure. Those skilled in the art will understand that the principles of this disclosure can be implemented in any suitably arranged system.

The increasing use of audio collection is one significant element that enables recent applications involving human-computer interactions. Audio collection is also important as part of audio-based health monitoring and analysis applications. Collection of audio from subjects is not only important for audio-based prediction, but also to train predictive algorithms, validate methods for larger scales of populations, and conduct deeper audio analysis in the cloud.

Capturing non-speech audio events and abnormal sounds corresponding to disease states and symptoms is increasingly important in passive health monitoring. For instance, a cough and its properties (e.g., frequency, intensity, type, and occurrence time) can be correlated with lung health condition. Audio features from speech (e.g., pause time, shimmer, and jitter) have also shown indication of lung obstruction. These features provide information in diagnosing and assessing obstructive and restrictive lung diseases and are considered as significant predictors of chronic obstructive pulmonary disease (COPD) exacerbation and asthmatic attacks.

The amount of continuous data available to be passively collected from subjects could facilitate detailed health analysis, early detection, and prevention of severe health conditions. Context information of the location, environment, and activity associated with the audio could be extracted as well, which in some cases can be correlated to the cause of change in health condition. Passive health monitoring can increase the compliance rate of subjects throughout the day since it can be achieved through minimum effort and interaction.

Current digital health platforms mainly rely on digital biomarkers collected from a mobile phone or wearable bio-sensors. Passive monitoring of non-speech sounds and non-private speech features would enable these digital health platforms to use more acoustic digital biomarkers (e.g., cough/sneeze frequency, breathing abnormalities, or the like). These features can be easily integrated with voice assistant applications which are already passively monitoring audio. Some of the benefits of continuous subject health tracking include continuous monitoring of speech features or patterns used as digital biomarkers (e.g., cognitive impairment or lung condition), longitudinal monitoring and tracking of (non-speech) symptoms, and early detection and prevention of adverse events (e.g., exacerbation of asthma attacks).

It has been recognized that continuous recording of audio raises audio privacy issues for subjects and for technology companies. For example, raw audio data can be used on the cloud for training, validating audio-based predictive algorithms, or deeper audio analysis. However, transferring of recorded audio containing private data to the cloud could potentially violate the privacy of the user. Therefore, there is a significant need to preserve privacy of subjects while continuously and passively collecting their audio on-device and/or before reaching the cloud or other entities that do not have permission to use the private audio data. Major elements in the audio data that are prone to risk of user privacy include private speech content, speaker identity, and third party (background) conversation.

In order to protect subject privacy, the subject's speech audio data can be obfuscated or replaced with an alternative such that the data is unintelligible and does not provide private information. However, current methods of privacy-preserved audio collection pose an implicit tradeoff with maintaining other non-private audio events and features that could be useful for post (on-cloud) data analysis. This non-private data that should be maintained includes, but is not limited to, the subject's speech features and non-speech audio events (e.g., cough, sneeze, throat clearing, and the like for health analysis) and environmental sound information (e.g., sounds from a park or busy street, which can be used for location context).

Thus, passive recording of audio poses a number of challenges. For example, speech content and subject identity are private information that may be captured or inferred by current methods of (privacy-preserved) audio collection. Speech segments may overlap with other audio activities in an uncontrolled recording environment with multiple speakers and background noises, which can result in misprediction of speech or non-speech. Current privacy-preserved audio collection (obfuscation) methods lack or have poor capability in distinguishing speech versus non-speech segments, and they potentially remove non-speech segments or unintentionally alter them such that useful features are lost and cannot be recovered for data analysis.

To address these and other issues, embodiments of this disclosure provide systems and methods for privacy-preserved audio collection or audio obfuscation. The disclosed embodiments maintain non-speech audio segments as well as non-private speech features of the original audio. In order to preserve privacy of subjects while continuously and passively collecting their audio on-device, the disclosed embodiments can be applied on the recorded audio before the violation of the privacy. The disclosed embodiments enable the automatic collection of non-private audio by eliminating the need for human review of the audio. The disclosed embodiments can be implemented on devices such as smart phones, wearables, or smart speakers. The obfuscated audio that does not contain the private information of subject identity and speech content can be transferred to the cloud for further usage and analysis.

FIG. 1 illustrates an example network configuration 100 in accordance with this disclosure. As shown in FIG. 1, according to embodiments of this disclosure, an electronic device 101 is included in the network configuration 100. The electronic device 101 may include at least one of a bus 110, a processor 120, a memory 130, an input/output (I/O) interface 150, a display 160, a communication interface 170, or a sensor 180. In some embodiments, the electronic device 101 may exclude at least one of the components or may add another component.

The bus 110 may include a circuit for connecting the components 120-180 with one another and transferring communications (such as control messages and/or data) between the components. The processor 120 may include one or more of a central processing unit (CPU), an application processor (AP), or a communication processor (CP). The processor 120 may perform control on at least one of the other components of the electronic device 101 and/or perform an operation or data processing relating to communication.

The memory 130 may include a volatile and/or non-volatile memory. For example, the memory 130 may store commands or data related to at least one other component of the electronic device 101. According to embodiments of this disclosure, the memory 130 may store software and/or a program 140. The program 140 may include, for example, a kernel 141, middleware 143, an application programming interface (API) 145, and/or an application program (or "application") 147. At least a portion of the kernel 141, middleware 143, or API 145 may be denoted an operating system (OS).

The kernel 141 may control or manage system resources (such as the bus 110, processor 120, or memory 130) used to perform operations or functions implemented in other programs (such as the middleware 143, API 145, or application program 147). The kernel 141 may provide an interface that allows the middleware 143, API 145, or application 147 to access the individual components of the electronic device 101 to control or manage the system resources. The middleware 143 may function as a relay to allow the API 145 or the application 147 to communicate data with the kernel 141, for example. A plurality of applications 147 may be provided. The middleware 143 may control work requests received from the applications 147, such as by allocating the priority of using the system resources of the electronic device 101 (such as the bus 110, processor 120, or memory 130) to at least one of the plurality of applications 147. The API 145 is an interface allowing the application 147 to control functions provided from the kernel 141 or the middleware 143. For example, the API 133 may include at least one interface or function (such as a command) for file control, window control, image processing, or text control.

The input/output interface 150 may serve as an interface that may, for example, transfer commands or data input from a user or other external devices to other component(s) of the electronic device 101. Further, the input/output interface 150 may output commands or data received from other component(s) of the electronic device 101 to the user or the other external devices.

The display 160 may include, for example, a liquid crystal display (LCD), a light emitting diode (LED) display, an organic light emitting diode (OLED) display, an active matrix OLED (AMOLED), a microelectromechanical systems (MEMS) display, or an electronic paper display. The display 160 can also be a depth-aware display, such as a multi-focal display. The display 160 may display various contents (such as text, images, videos, icons, or symbols) to the user. The display 160 may include a touchscreen and may receive, for example, a touch, gesture, proximity, or hovering input using an electronic pen or a body portion of the user.

The communication interface 170 may set up communication between the electronic device 101 and an external electronic device (such as a first electronic device 102, a second electronic device 104, or a server 106). For example, the communication interface 170 may be connected with a network 162 or 164 through wireless or wired communication to communicate with the external electronic device.

The electronic device 101 further includes one or more sensors 180 that can meter a physical quantity or detect an activation state of the electronic device 101 and convert metered or detected information into an electrical signal. For example, one or more sensors 180 can include one or more buttons for touch input, one or more cameras, a gesture sensor, a gyroscope or gyro sensor, an air pressure sensor, a magnetic sensor or magnetometer, an acceleration sensor or accelerometer, a grip sensor, a proximity sensor, a color sensor (such as a red green blue (RGB) sensor), a bio-physical sensor, a temperature sensor, a humidity sensor, an illumination sensor, an ultraviolet (UV) sensor, an electromyography (EMG) sensor, an electroencephalogram (EEG) sensor, an electrocardiogram (ECG) sensor, an infrared (IR) sensor, an ultrasound sensor, an iris sensor, or a fingerprint sensor. The sensor(s) 180 can also include an inertial measurement unit, which can include one or more accelerometers, gyroscopes, and other components. The sensor(s) 180 can further include a control circuit for controlling at least one of the sensors included here. Any of these sensor(s) 180 can be located within the electronic device 101.

The first external electronic device 102 or the second external electronic device 104 may be a wearable device or an electronic device 101-mountable wearable device (such as a head mounted display (HMD)). When the electronic device 101 is mounted in an HMD (such as the electronic device 102), the electronic device 101 may detect the mounting in the HMD and operate in a virtual reality mode. When the electronic device 101 is mounted in the electronic device 102 (such as the HMD), the electronic device 101 may communicate with the electronic device 102 through the communication interface 170. The electronic device 101 may be directly connected with the electronic device 102 to communicate with the electronic device 102 without involving with a separate network.

The wireless communication may use at least one of, for example, long term evolution (LTE), long term evolution-advanced (LTE-A), code division multiple access (CDMA), wideband code division multiple access (WCDMA), universal mobile telecommunication system (UMTS), wireless broadband (WiBro), or global system for mobile communication (GSM), as a cellular communication protocol. The wired connection may include at least one of, for example, universal serial bus (USB), high definition multimedia interface (HDMI), recommended standard 232 (RS-232), or plain old telephone service (POTS). The network 162 may include at least one communication network, such as a computer network (like a local area network (LAN) or wide area network (WAN)), the Internet, or a telephone network.

The first and second external electronic devices 102 and 104 each may be a device of the same type or a different type from the electronic device 101. According to embodiments of this disclosure, the server 106 may include a group of one or more servers. Also, according to embodiments of this disclosure, all or some of the operations executed on the electronic device 101 may be executed on another or multiple other electronic devices (such as the electronic devices 102 and 104 or server 106). Further, according to embodiments of this disclosure, when the electronic device 101 should perform some function or service automatically or at a request, the electronic device 101, instead of executing the function or service on its own or additionally, may request another device (such as electronic devices 102 and 104 or server 106) to perform at least some functions associated therewith. The other electronic device (such as electronic devices 102 and 104 or server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technique may be used, for example.

While FIG. 1 shows that the electronic device 101 includes the communication interface 170 to communicate with the external electronic device 102 or 104 or server 106 via the network(s) 162 and 164, the electronic device 101 may be independently operated without a separate communication function, according to embodiments of this disclosure. Also, note that the electronic device 102 or 104 or the server 106 could be implemented using a bus, a processor, a memory, an I/O interface, a display, a communication interface, and an event processing module (or any suitable subset thereof) in the same or similar manner as shown for the electronic device 101.

Although FIG. 1 illustrates one example of a network configuration 100, various changes may be made to FIG. 1. For example, the network configuration 100 could include any number of each component in any suitable arrangement. In general, computing and communication systems come in a wide variety of configurations, and FIG. 1 does not limit the scope of this disclosure to any particular configuration. Also, while FIG. 1 illustrates one operational environment in which various features disclosed in this patent document can be used, these features could be used in any other suitable system.

Figure 2:
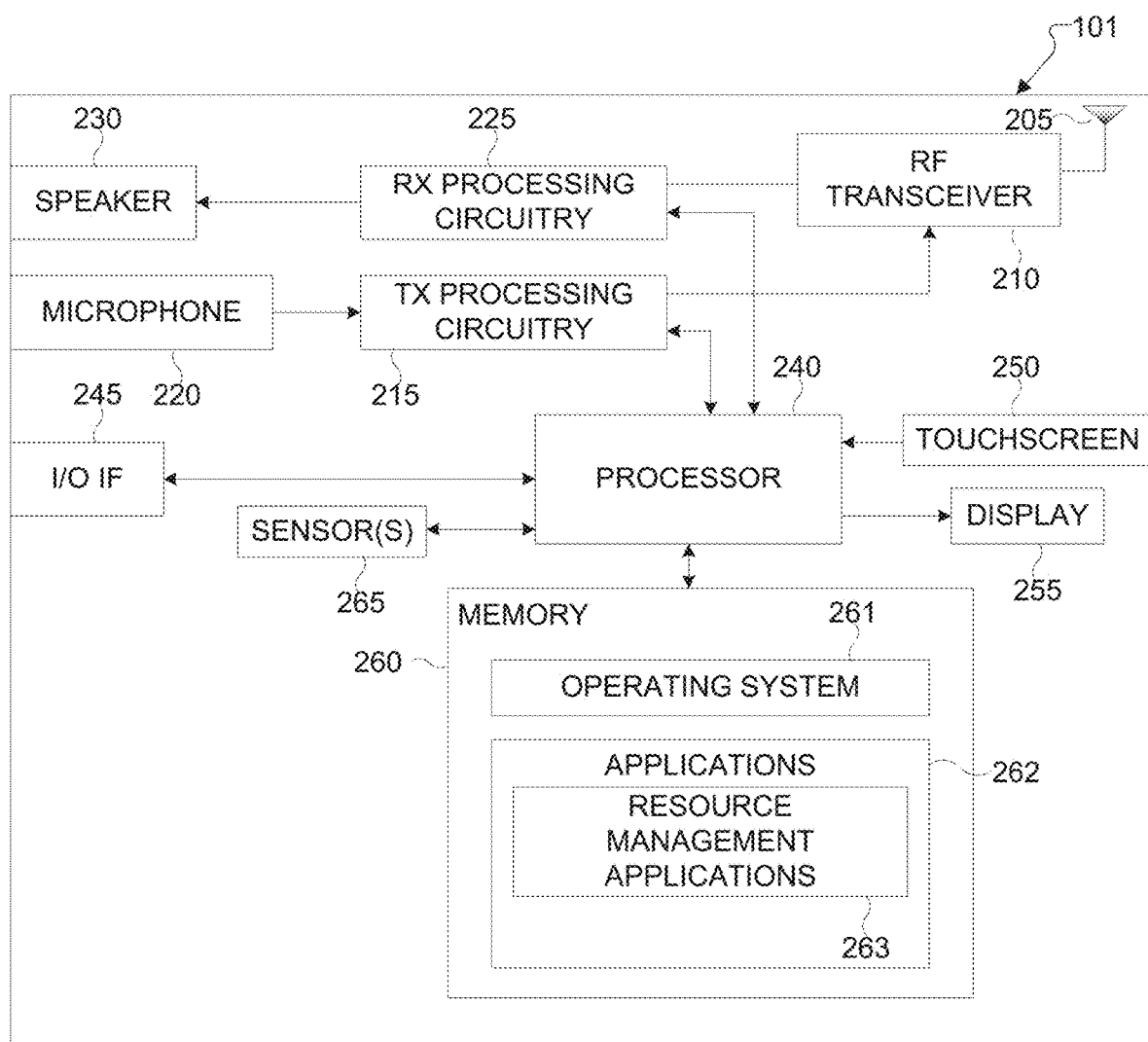
FIG. 2 illustrates an example electronic device in accordance with this disclosure.

FIG. 2 illustrates an example electronic device 101 in accordance with this disclosure. The electronic device 101 could represent one or more of the electronic devices 101, 102, or 104 in FIG. 1. As shown in FIG. 2, the electronic device 101 includes an antenna 205, a radio frequency (RF) transceiver 210, transmit (TX) processing circuitry 215, a microphone 220, and receive (RX) processing circuitry 225. The electronic device 101 also includes a speaker 230, a processor 240, an input/output (I/O) interface (IF) 245, an input 250, a display 255, and a memory 260. The memory 260 includes an operating system (OS) program 261 and one or more applications 262.

The RF transceiver 210 receives, from the antenna 205, an incoming RF signal transmitted by another component in a system. The RF transceiver 210 down-converts the incoming RF signal to generate an intermediate frequency (IF) or baseband signal. The IF or baseband signal is sent to the RX processing circuitry 225, which generates a processed baseband signal by filtering, decoding, and/or digitizing the baseband or IF signal. The RX processing circuitry 225 transmits the processed baseband signal to the speaker 230 (such as for voice data) or to the processor 240 for further processing.

The TX processing circuitry 215 receives analog or digital voice data from the microphone 220 or other outgoing baseband data (such as web data, e-mail, or interactive video game data) from the processor 240. The TX processing circuitry 215 encodes, multiplexes, and/or digitizes the outgoing baseband data to generate a processed baseband or IF signal. The RF transceiver 210 receives the outgoing processed baseband or IF signal from the TX processing circuitry 215 and up-converts the baseband or IF signal to an RF signal that is transmitted via the antenna 205.

The processor 240 can include one or more processors or other processors and execute the OS program 261 stored in the memory 260 in order to control the overall operation of the electronic device 101. For example, the processor 240 could control the reception of forward channel signals and the transmission of reverse channel signals by the RF transceiver 210, the RX processing circuitry 225, and the TX processing circuitry 215 in accordance with well-known principles. In some embodiments, the processor 240 includes at least one microprocessor or microcontroller.

The processor 240 is also capable of executing other processes and programs resident in the memory 260. The processor 240 can move data into or out of the memory 260 as required by an executing process. In some embodiments, the processor 240 is configured to execute the applications 262 based on the OS program 261 or in response to signals received from external devices or an operator. The processor 240 can execute a resource management application 263 for monitoring system resources. The processor 240 is also coupled to the I/O interface 245, which provides the electronic device 101 with the ability to connect to other devices such as laptop computers, handheld computers and other accessories, for example, a virtual reality (VR) headset. The I/O interface 245 is the communication path between these accessories and the processor 240. The processor 240 can recognize accessories that are attached through the I/O interface 245, such as a VR headset connected to a USB port.

The processor 240 is also coupled to the input 250 and the display 255. The operator of the electronic device 101 can use the input 250 (e.g., keypad, touchscreen, button etc.) to enter data into the electronic device 101. The display 255 may be an LCD, LED, OLED, AMOLED, MEMS, electronic paper, or other display capable of rendering text and/or at least limited graphics, such as from web sites.

The memory 260 is coupled to the processor 240. Part of the memory 260 could include a random access memory (RAM), and another part of the memory 260 could include a Flash memory or other read-only memory (ROM).

The electronic device 101 further includes one or more sensors 265 that can meter a physical quantity or detect an activation state of the electronic device 101 and convert metered or detected information into an electrical signal. For example, the sensor 265 may include any of the various sensors 180 discussed above.

Although FIG. 2 illustrates one example of an electronic device 101, various changes may be made to FIG. 2. For example, various components in FIG. 2 could be combined, further subdivided, or omitted and additional components could be added according to particular needs. As a particular example, the processor 240 could be divided into multiple processors, such as one or more central processing units (CPUs) and one or more graphics processing units (GPUs). Also, while FIG. 2 illustrates the electronic device 101 configured as a mobile telephone or smart phone, electronic devices could be configured to operate as other types of mobile or stationary devices. In addition, as with computing and communication networks, electronic devices can come in a wide variety of configurations and FIG. 2 does not limit this disclosure to any particular electronic device.

Figure 3:
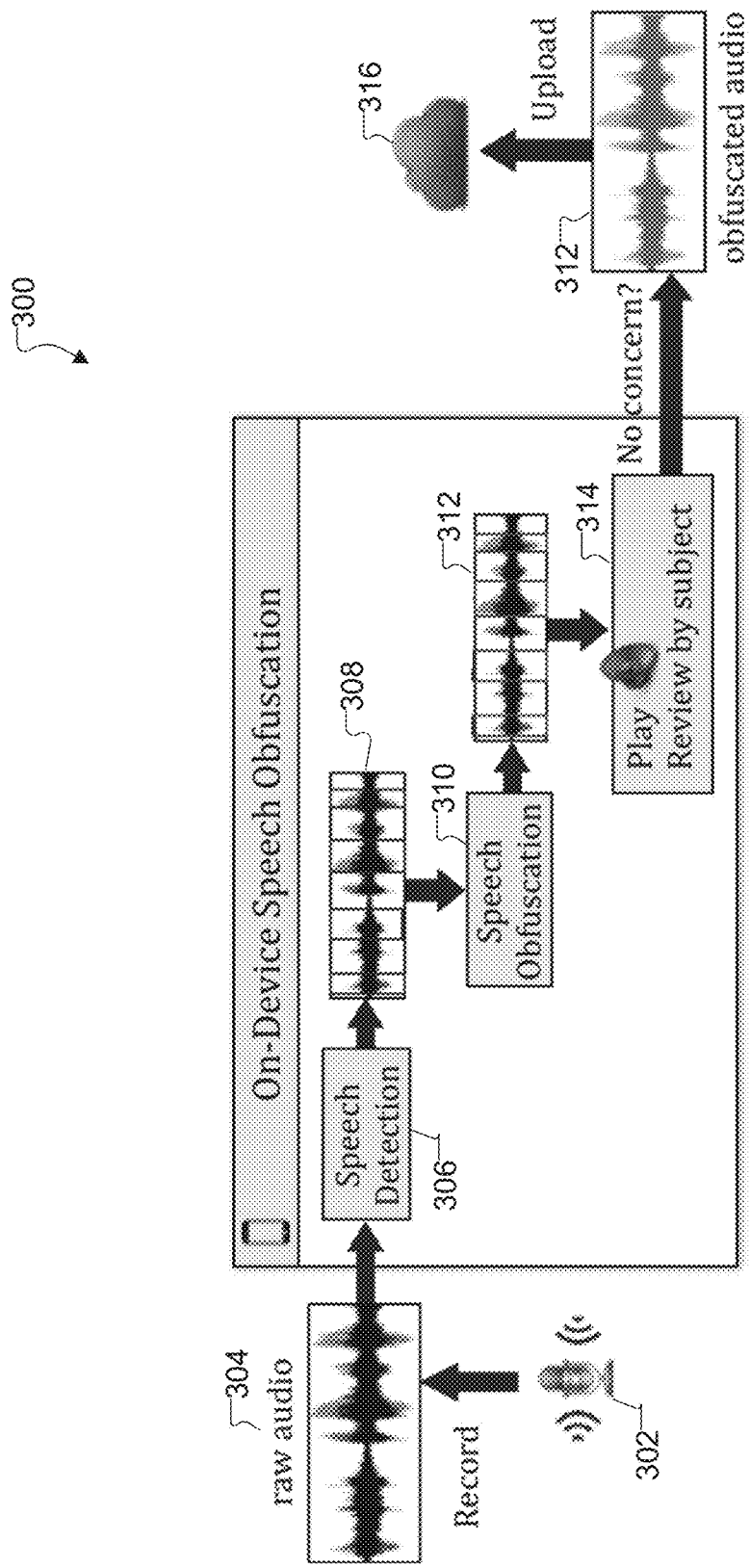
FIG. 3 illustrates an example process for generating obfuscated audio in accordance with this disclosure.

FIG. 3 illustrates an example process 300 for generating obfuscated audio in accordance with this disclosure. For ease of explanation, the process 300 is described as involving at least one electronic device (such as the electronic device 101 of FIG. 1). However, the process 300 could be used with any other suitable device or system without departing from the scope of this disclosure. Certain operations of the process 300 are presented here at a general level. Further details of the process 300 are provided below in conjunction with other figures.

As shown in FIG. 3, a microphone 302 or other audio sensor is used to record raw audio 304 for an arbitrary period of time. For example, the electronic device can use a built-in microphone 302 to record audio associated with a user of the electronic device. The audio can include speech spoken by the user and/or people in proximity to the user, non-speech sounds generated by the user and/or people in proximity to the user, background noises and speech that occur around the user, or a combination of these.

The electronic device performs a speech detection function 306 to detect and identify one or more speech samples 308 in the raw audio 304. The speech samples 308 correspond to speech spoken by the user and/or people in proximity to the user. In identifying the speech samples 308, the electronic device utilizes a speech presence scoring technique that distinguishes between audio activities containing speech, non-speech, or noisy speech (i.e., speech that overlaps with non-speech background sounds). The speech presence scoring technique combines features from frames within an audio window and maps the features so as to become more independent of the recording settings and audio context. The electronic device also periodically generates a background noise profile by statistically analyzing the level of speech, non-speech, or background noise present in the audio window.

Once the speech samples 308 are identified and distinguished from the background noises, the electronic device performs a speech obfuscation function 310 to convert the speech samples 308 to obfuscated speech samples 312. In some embodiments, the electronic device uses the background noise profile to adapt the classification and speech obfuscation function 310 to changing recording environments. The speech obfuscation function 310 maintains non-speech audio segments without modification, and obfuscates the identified speech samples 308 by conditionally generating synthetic speech audio that maintains non-private speech features and preserves its audio characteristics of human speech. In performing the speech obfuscation function 310, the electronic device operates to maintain as much non-private data as possible that could be used in audio-based analysis applications, such as health monitoring.

In some embodiments, once the obfuscated speech samples 312 are generated by the electronic device, the obfuscated speech samples 312 can be played and reviewed by the user in a review operation 314 to determine if there are any privacy concerns. This is optional; in some embodiments, the obfuscated speech samples 312 may not be reviewed by the user. If there are no concerns, then the electronic device can upload the obfuscated speech samples 312 to a device in the cloud 316, such as the server 106 in FIG. 1, where the samples 312 can be used for audio-based analysis applications.

Although FIG. 3 illustrates one example of a process 300 for generating obfuscated audio, various changes may be made to FIG. 3. For example, various operations in FIG. 3 could overlap, occur in parallel, occur in a different order, or occur any number of times. Also, the various functions and operations shown and described above with respect to FIG. 3 can be implemented in the electronic device (which could include any of the electronic devices 101, 102, 104 or the server 106) in any suitable manner. For example, in some embodiments, at least some of the functions and operations can be implemented or supported using one or more software applications or other software instructions that are executed by the processor(s) 120, 240 of the electronic device(s). In other embodiments, at least some of the functions and operations can be implemented or supported using dedicated hardware components. In general, the functions and operations can be performed using any suitable hardware or any suitable combination of hardware and software/firmware instructions. In general, computing and communication systems come in a wide variety of configurations, and FIG. 3 does not limit the scope of this disclosure to any particular configuration.

Figure 4:
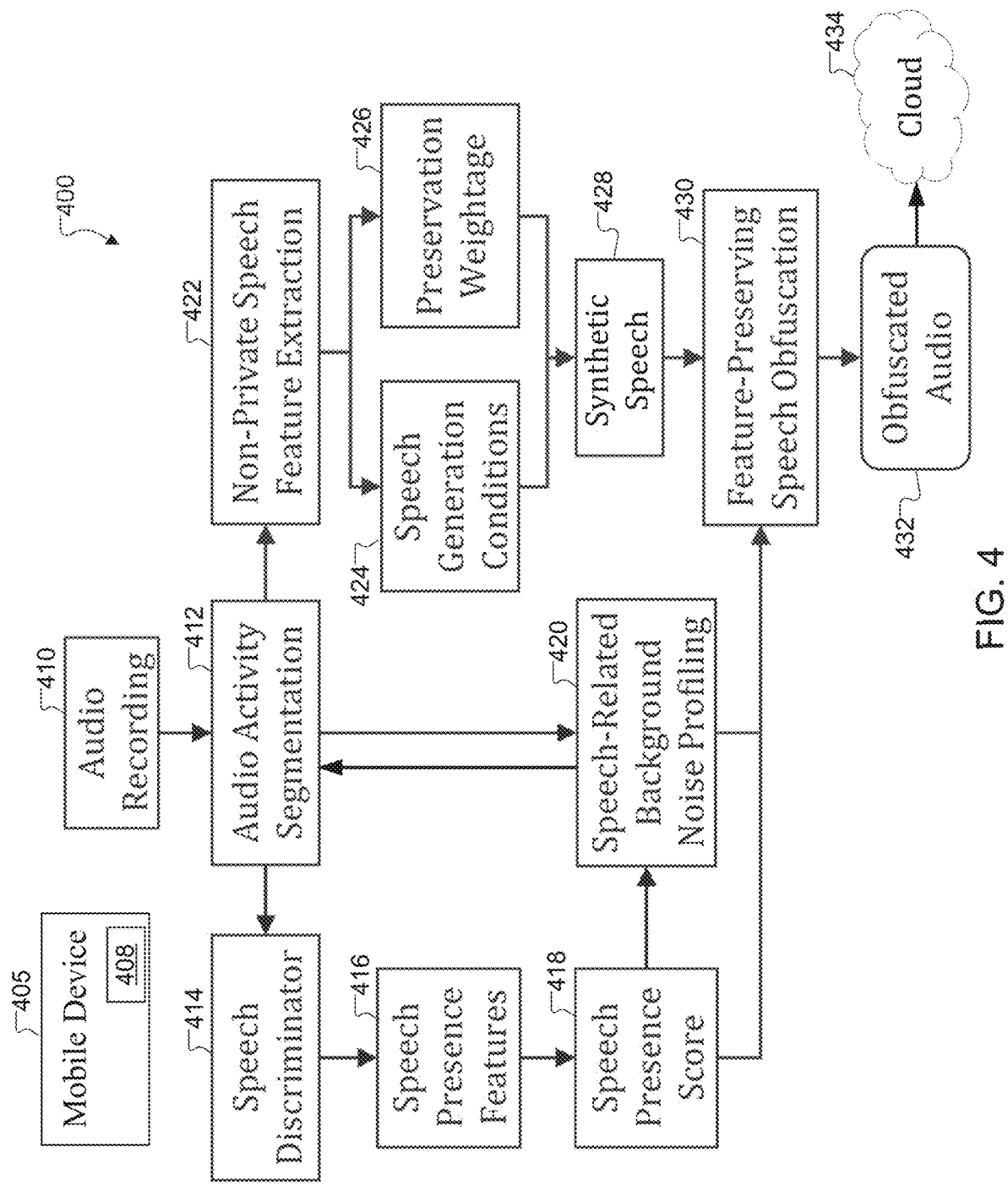
FIG. 4 illustrates an example process for continuous, on-device, privacy-preserved collection of audio in accordance with this disclosure.

FIG. 4 illustrates an example process 400 for continuous, on-device, privacy-preserved collection of audio in accordance with this disclosure. For ease of explanation, the process 400 is described as involving the process 300 shown in FIG. 3. However, the process 400 could involve any other suitable process and be used in any suitable system without departing from the scope of this disclosure.

As shown in FIG. 4, the process 400 is performed by a mobile device 405. The mobile device 405 is a mobile electronic device that is associated with (or used by) a user who may be interested in health monitoring. The mobile device 405 may represent one of the electronic devices 101, 102, 104 of FIG. 1. For example, the mobile device 405 may be the user's smart phone, smart watch, or tablet. The mobile device 405 can include one or more audio sensors 408 that are capable of detecting and recording audio in the vicinity of the mobile device 405, such as the microphone 220 of FIG. 2.

To collect data that can be used for audio-based analysis applications, the mobile device 405 performs an audio recording function 410 to generate a raw audio recording. In some embodiments, the audio recording function 410 can represent the recording of the raw audio 304 of FIG. 3. The audio recording function 410 can include detection and recording by the audio sensor 408 of sounds associated with the user and sounds surrounding the user. Specifically, this can include the audio sensor 408 detecting sounds emanating from the user while the user breathes, coughs, or wheezes. The audio sensor 408 can also detect speech that is spoken by the user and/or people in proximity to the user, and can further detect other noises, such as background noise surrounding the user.

After the audio recording is generated, the mobile device 405 performs an audio activity segmentation function 412, in which the mobile device 405 traverses the audio recording and separates audio activities (which can include speech or non-speech) from silence or background noise based on energy level, volume, or other audio parameters. The audio activity segmentation function 412 generates a list of audio activities. The audio activity segmentation function 412 represents any suitable algorithm or process that is capable of separating audio activities from silent or background noise. In some embodiments, the audio activities can be labeled with a '1' and periods of silence or mere background noise can be labeled with a '0'. Of course, this is merely one example; other identification and labeling schemes can be used and are within the scope of this disclosure.

After the audio activities are separated from silence or background noise, the mobile device 405 analyzes the audio activities to determine the presence of human speech in the audio activities. First, the mobile device 405 executes a speech discriminator module 414 to analyze all audio frames within each audio activity. As used herein, an audio frame is a short duration (e.g., 20-250 milliseconds) portion of a comparatively longer audio activity (which can vary in length and may be 2-5 seconds or longer). The speech discriminator module 414 comprises an already-trained unsupervised machine learning model that captures and extracts speech audio characteristics in each audio activity. During operation, the speech discriminator module 414 generates a set of speech presence features 416 for each audio activity, which can include:

$h_{mean}, h_{max}, h_{min}, h_{var}, a, e$ where h is the likelihood distance of each audio frame from speech audio characteristics, a is the maximum amplitude of the audio activity, and e is the maximum energy of the audio activity. The h values for audio frames in each audio activity are used to extract the above features.

The mobile device 405 combines and maps the generated speech presence features 416 to determine a speech presence score 418 for the corresponding audio activity. In some embodiments, the mobile device 405 uses the speech presence features 416 as inputs to a machine learning model f, like a linear regression or decision tree, to determine the speech presence score 418. In some embodiments, the machine learning model is trained using training examples of the speech presence features 416 and the labeled audio data. The machine learning model maps the speech presence features 416 to the speech presence score 418 as follows:

$$s = f(h_{mean}, h_{max}, h_{min}, h_{var}, a, e)$$

where s represents the speech presence score 418.

The speech presence score 418 can be a scalar score (discrete or continuous) in the range of [0-2], with values indicating the following:

'0'—only non-speech audio;
'1'—noisy speech (speech overlapping with non-speech);
'2'—only speech audio.

The speech presence score 418 enables the distinguishing of audio classes for different purposes in the privacy-preserved audio collection. For example, as discussed in greater detail below, speech audio ('2') may be obfuscated, but useful for non-private speech feature extraction; non-speech audio ('0') may be maintained without modification for extracting non-private audio data; and noisy speech audio ('1') may be obfuscated, but not useful for non-private speech feature extraction due to potentially invalid values.

The use of the speech presence score 418 as disclosed herein is advantageous over existing speech classification methods that have limited predefined audio classes (e.g., voice vs. silence, speech vs. cough, etc.) and would cause uncertain predictions against general and unknown non-speech audio classes. For example, automatic speech recognition (ASR) methods assume the presence of speech within the recorded audio; this is typically due to the fact that the speech recognition is triggered after detection of a predefined "wake-up" command. Typical ASR methods process the audio and map it to the highest probable text regardless of the actual presence of speech. Such methods introduce excessive speech detection errors in uncontrolled recording environments where other sources of audio are present. For instance, some current voice assistants would continue listening after the "wake-up" command while non-speech sounds are received.

In contrast, the speech presence score 418 provides a robust score that is independent of what recording device is used to record the audio, how distant the audio source is from the recording device, or the volume of the audio. The speech presence score 418 is also independent of environment audio context (e.g., what other noises are present in the environment), speech text/content (e.g., subject matter of speech, spoken language, dialect, accent, and the like), and non-speech audio class.

After the speech presence score 418 is determined for each audio activity, the mobile device 405 operates to reduce the effect of background noise on speech detection. In general, it has been observed that the estimation accuracy of speech detection algorithms can be significantly affected by the presence of background noises and other speakers' conversations in the background. This can lead to high numbers of false positives and/or false negatives. For instance, voice assistants may continue listening if there is a constant background TV noise, even when the user stops talking (as described above).

To address this, the mobile device 405 periodically performs statistical analysis of the values of the speech presence scores 418 and determines how much speech-related noise is present in the background. This information is used to create a speech-related background noise profile 420. The background noise profile 420 provides statistical information of how close the audio activities and background noise are to speech audio patterns. In particular, the background noise profile 420 provides a speech discrimination threshold, which can be used to better distinguish each audio activity as containing speech, non-speech, or noisy speech.

Figure 5:
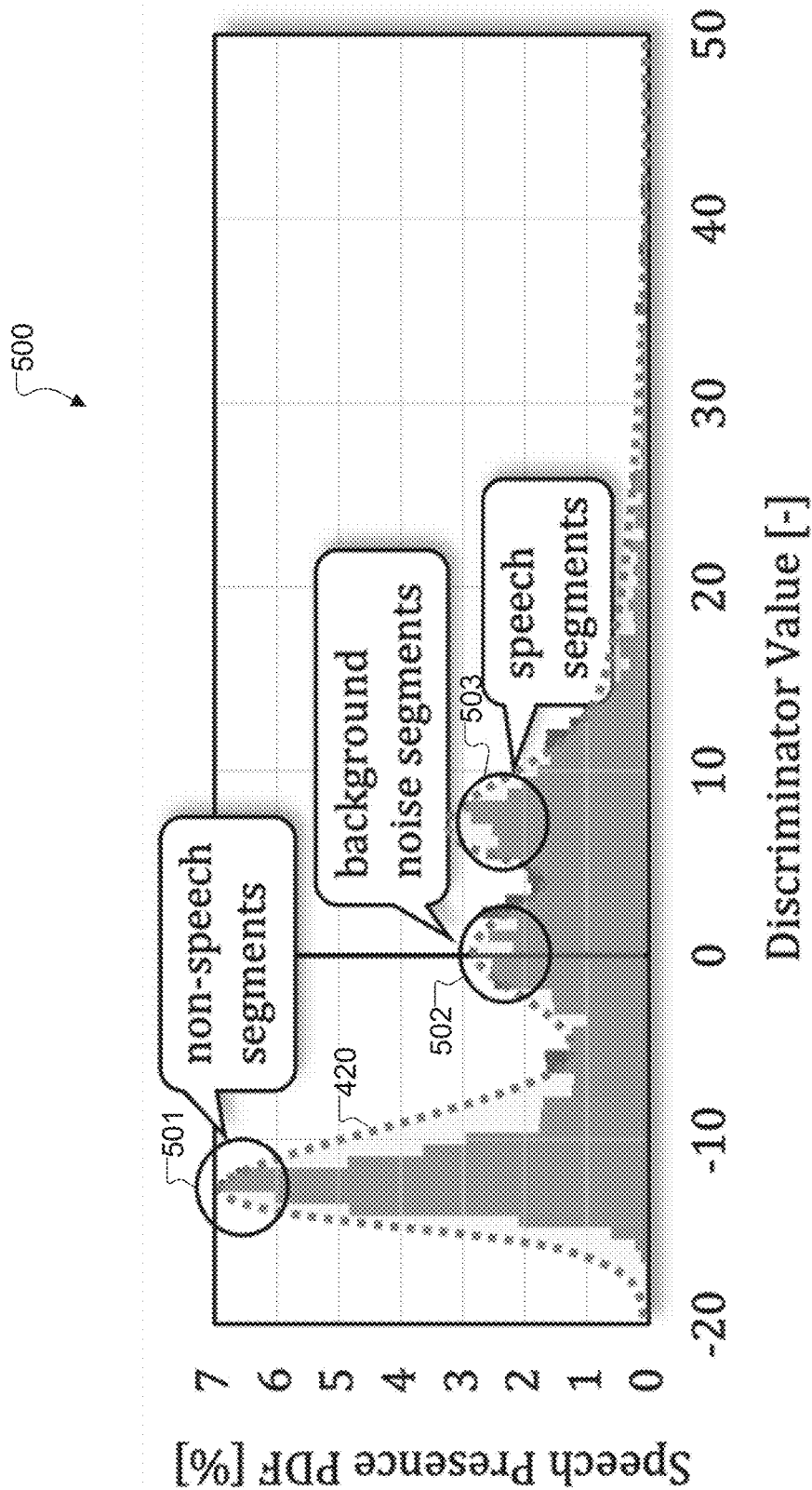
FIG. 5 illustrates an example chart showing a background noise profile in accordance with this disclosure.

FIG. 5 illustrates an example chart 500 showing a background noise profile 420 in accordance with this disclosure. As shown in FIG. 5, the chart 500 shows the background noise profile 420 as a probability density function (PDF) of human speech presence in a two minute audio sample. The background noise profile 420 is a histogram that includes three main peaks 501-503. The peak 501 represents non-speech audio, which has the lowest discriminator value. The peak 502 represents silent or background noise audio. The peak 503 represents speech audio, which has the highest discriminator value.

The level and distribution of noise among speech, non-speech, or silence audio segments can be extracted from the background noise profile 420. For example, the mobile device 405 can analyze the background noise profile 420 using a clustering algorithm such as k-mean to extract the peaks 501-503. The average of the low peak 501 and the middle peak 502 should maintain specific values, which are mainly constant for non-speech or silent segments. These values may be shifted to right by the presence of background noises that are similar to speech, or shifted to the left by the presence of background noises that are similar to non-speech. This shift in average values of the peaks 501-503 is calculated in the background noise profile 420 and then used to adjust the speech discrimination threshold for obfuscation. The recording environments may change over time, so the mobile device 405 can regenerate the background noise profile 420 periodically (e.g., every 15-20 seconds) to adapt to the change of environment. This would enable a seamless speech obfuscation during continuous audio recording for different environments. The background noise profile 420 can be stored as well for later analysis of environmental context information.

The background noise profile 420 can also be used to improve the audio activity segmentation function 412. For example, the mobile device 405 can use the background noise profile 420 to adjust speech detection with respect to noise level from background human conversation or non-speech abrupt sounds.

After the background noise profile 420 is determined, the mobile device 405 operates to obscure private speech features in the audio activities. In general, it has been observed that current methods of privacy-preserved audio collection or obfuscation have implicit trade-offs where they either cannot maintain the audio privacy with high speech intelligibility or may unintentionally remove or change the non-private audio data that are useful for data analysis.

To address this, the mobile device 405 operates to remove speech content and speaker identity by replacing the private speech segments with non-private synthetic speech segments. Use of non-private synthetic speech segments maintains non-speech audio segments, audio characteristics of natural speech, and non-private speech features of original audio, such as shimmer and jitter. The maintenance of non-private audio data and generation of synthetic speech segments enhances the capability of utilizing the raw non-speech data or hidden non-private speech features for data analysis in applications such as health assessment.

It is noted that non-speech audio segments (e.g., silence, background noises, coughs, sneezes, wheezes, and the like) are maintained by the mobile device 405 during speech obfuscation. In particular, the mobile device 405 maintains the audio activities with a speech presence score 418 of '0'. The non-speech audio segments provide useful context for environment sound classification and other applications (e.g., lung health assessments). Keeping the non-speech audio segments in the obfuscated audio helps to maintain temporal characteristics of the audio, e.g., the location of speech segments in the audio, or with respect to other segments, and the pause time between each segments.

In one operation of speech obfuscation, the mobile device 405 performs a non-private speech feature extraction function 422, in which non-private speech features (e.g., shimmer, jitter, and the like) are extracted from the speech segments. The non-private speech features can be useful for speech-based analyses, such as vocal cord dysfunction and obstruction severity prediction. The non-private speech features are also used to generate synthetic speech segments which maintain the non-private speech features.

The non-private speech features are used in determining speech generation conditions 424, which are values that adjust the objective of a synthetic speech generation module 428. One or more preservation weightages 426 are also defined based on the non-private speech features to calculate scores for similarity of synthetic speech segments to the original segments quantifying their maintenance of the non-private speech features, and to rank and select the closest one.

The synthetic speech generation module 428 is an already-trained unsupervised machine learning model that captures speech audio characteristics and generates synthetic speech segments as an output. The generated synthetic speech segments have similar audio characteristics to a natural human speech. The mobile device 405 executes the synthetic speech generation module 428 to generate the synthetic speech segments.

Figure 6:
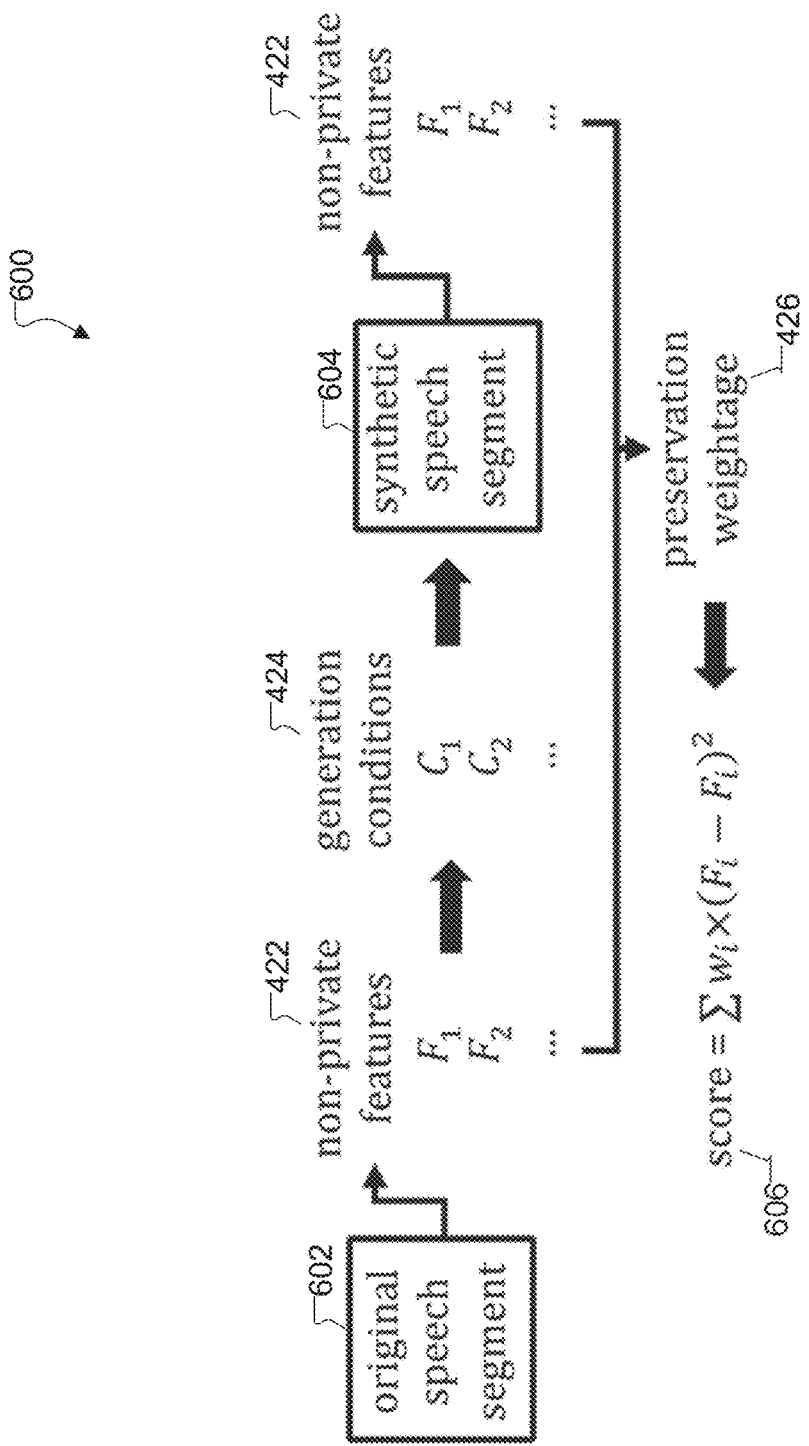
FIG. 6 illustrates an example process for generating synthetic speech segments using a synthetic speech generation module in accordance with this disclosure.

FIG. 6 illustrates an example process 600 for generating synthetic speech segments using the synthetic speech generation module 428 in accordance with this disclosure. As shown in FIG. 6, the non-private speech feature extraction function 422 is executed to extract non-private speech features from an original speech segment 602. The non-private speech features are used in determining the speech generation conditions 424. Using the speech generation conditions 424, the synthetic speech generation module 428 then generates the synthetic speech segments 604. The preservation weightages 426 are used to calculate scores 606 for similarity of synthetic speech segments 604 to the original segments 602 quantifying their maintenance of the non-private speech features, and to rank and select the closest one. The score values are evaluated to select the synthetic speech segments.

Turning again to FIG. 4, after the synthetic speech segments are generated using the synthetic speech generation module 428, the mobile device 405 performs a feature-preserving speech obfuscation function 430 to generate an obfuscated audio recording 432. In the feature-preserving speech obfuscation function 430, the original speech segments are replaced with the synthetic speech segments, which obfuscate the speech content and user identity. Each selected synthetic speech segment replaces a corresponding original speech segment. As noted above, the generated synthetic speech segments have similar audio characteristics to natural human speech. Also, the obfuscated audio recording 432 maintains the non-private features of the original audio, which is useful for post audio data analysis. Therefore, the obfuscated audio recording 432 can be later processed in an end-to-end audio-based predictive algorithm or application since it maintains the class type.

In some embodiments, the mobile device 405 uploads or sends the obfuscated audio recording 432 to a device in the cloud 434, such as the server 106 in FIG. 1, which extends the capability of maintaining a wider range of non-private features using a raw audio sample that also represents the original speech segment and its distribution.

Although FIG. 4 illustrates one example of a process 400 for continuous, on-device, privacy-preserved collection of audio, various changes may be made to FIG. 4. For example, various operations in FIG. 4 could overlap, occur in parallel, occur in a different order, or occur any number of times. Also, the various functions and operations shown and described above with respect to FIG. 4 can be implemented in the mobile device 405 or a combination of devices in any suitable manner. In general, the functions and operations can be performed using any suitable hardware or any suitable combination of hardware and software/firmware instructions.

Figure 7:
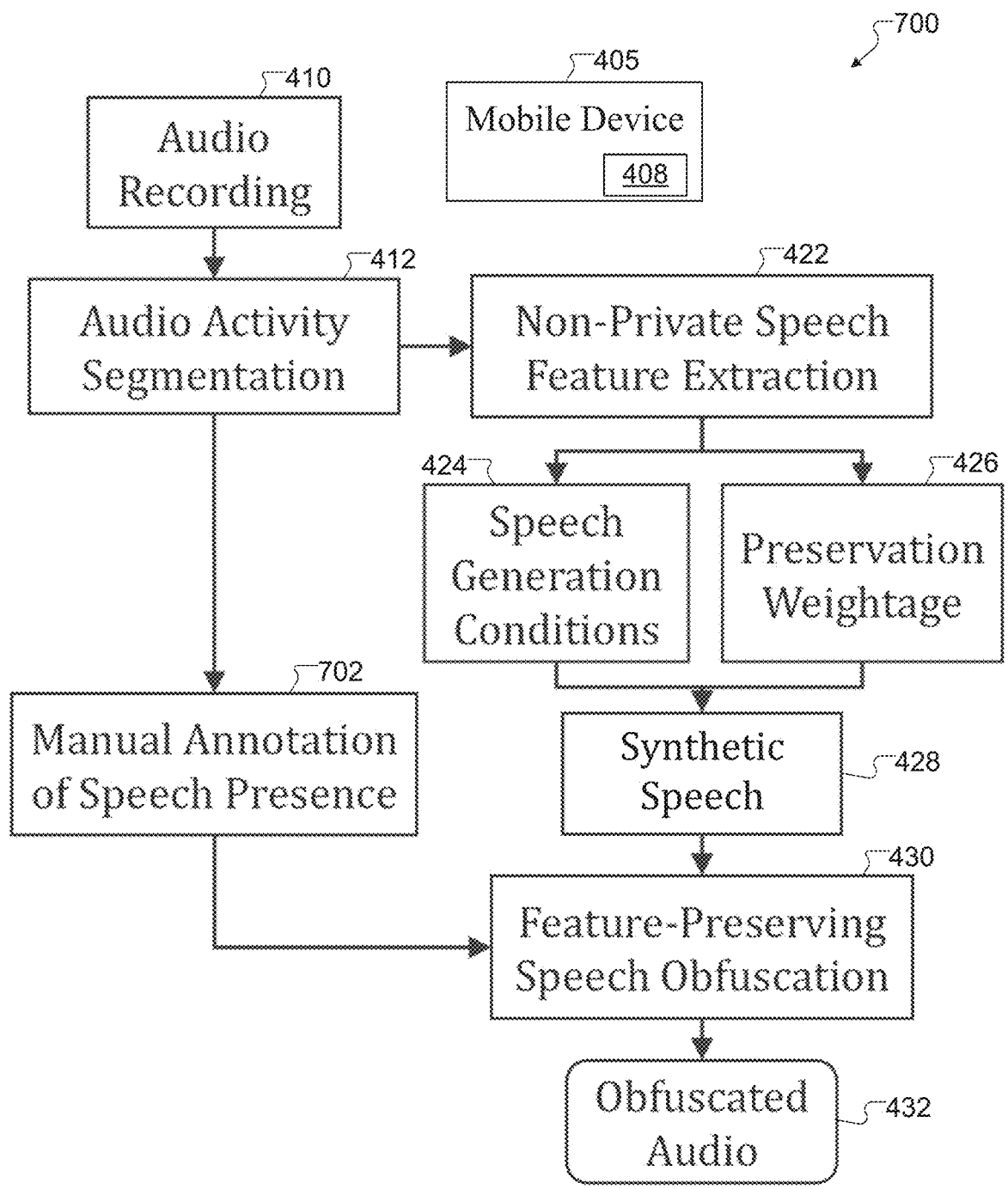
FIG. 7 illustrates another example process for continuous, on-device, privacy-preserved collection of audio in accordance with this disclosure.

FIG. 7 illustrates another example process 700 for continuous, on-device, privacy-preserved collection of audio in accordance with this disclosure. For ease of explanation, the process 700 is described as a variation of the process 400 shown in FIG. 4. However, the process 700 could involve any other suitable process and be used in any suitable system without departing from the scope of this disclosure.

As shown in FIG. 7, the process 700 includes a number of components and operations that are the same as or similar to corresponding components and operations of the process 400. In contrast to the process 400 (in which the mobile device 405 automatically generates the speech presence score 418), the process 700 includes a manual annotation operation 702 for annotation of audio activities.

During the manual annotation operation 702, a reviewer listens to the audio segments and manually provides input on the presence of speech, non-speech, or noisy speech. For example, the reviewer could actuate a control or button in a user interface whenever the reviewer hears speech, non-speech, or noisy speech in the audio segments. Each input can assign one or more labels to the audio segments, where each label associates the audio segment with speech, non-speech, or noisy speech. The labels are then used by the mobile device 405 to select which audio segments need to be obfuscated, maintained, or used for feature extraction. For example, the mobile device 405 can use the labels to create generation conditions 424 and preservation weightages 426, generate synthetic speech segments, and to obfuscate the audio the same as, or similar to, the process 400 of FIG. 4.

Although FIG. 7 illustrates one example of a process 700 for continuous, on-device, privacy-preserved collection of audio, various changes may be made to FIG. 7. For example, various operations in FIG. 7 could overlap, occur in parallel, occur serially, occur in a different order, or occur any number of times.

Figure 8:
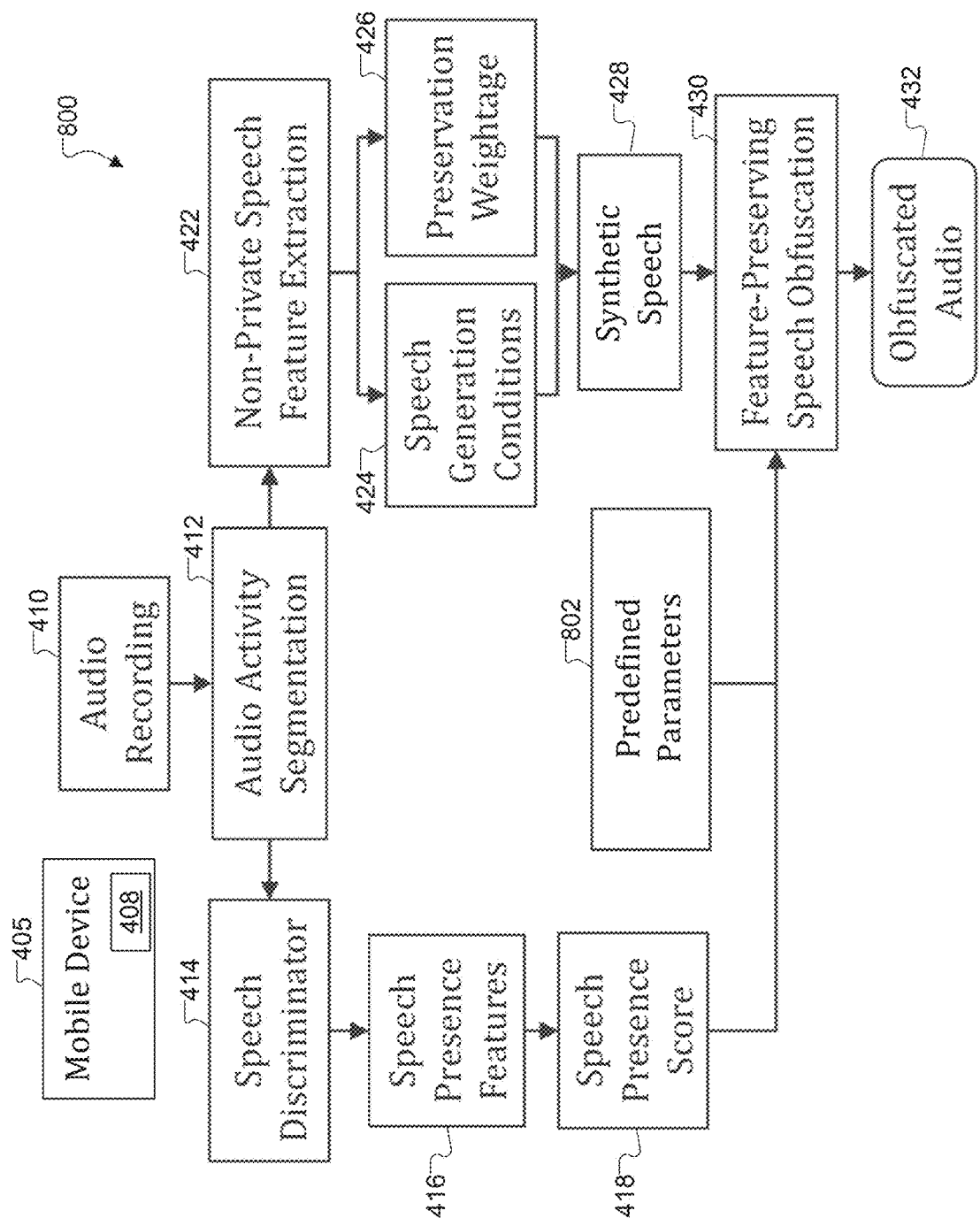
FIG. 8 illustrates yet another example process for continuous, on-device, privacy-preserved collection of audio in accordance with this disclosure.

FIG. 8 illustrates yet another example process 800 for continuous, on-device, privacy-preserved collection of audio in accordance with this disclosure. For ease of explanation, the process 800 is described as a variation of the process 400 shown in FIG. 4. However, the process 800 could involve any other suitable process and be used in any suitable system without departing from the scope of this disclosure.

As shown in FIG. 8, the process 800 includes a number of components and operations that are the same as or similar to corresponding components and operations of the process 400. In contrast to the process 400 (in which the mobile device 405 generates the background noise profile 420), the process 800 includes predefined parameters 802 that are used instead of a background noise profile. The predefined parameters 802 comprise one or more statistically defined and tuned parameters that can be used to separate speech and non-speech segments. The predefined parameters 802 can be determined in advance for a specific recording and environment. The mobile device 405 can use the predefined parameters 802 for distinguishing between speech and non-speech before performing the feature-preserving speech obfuscation the same as, or similar to, the process 400 of FIG. 4.

Although FIG. 8 illustrates one example of a process 800 for continuous, on-device, privacy-preserved collection of audio, various changes may be made to FIG. 8. For example, various operations in FIG. 8 could overlap, occur in parallel, occur serially, occur in a different order, or occur any number of times.

Figure 9:
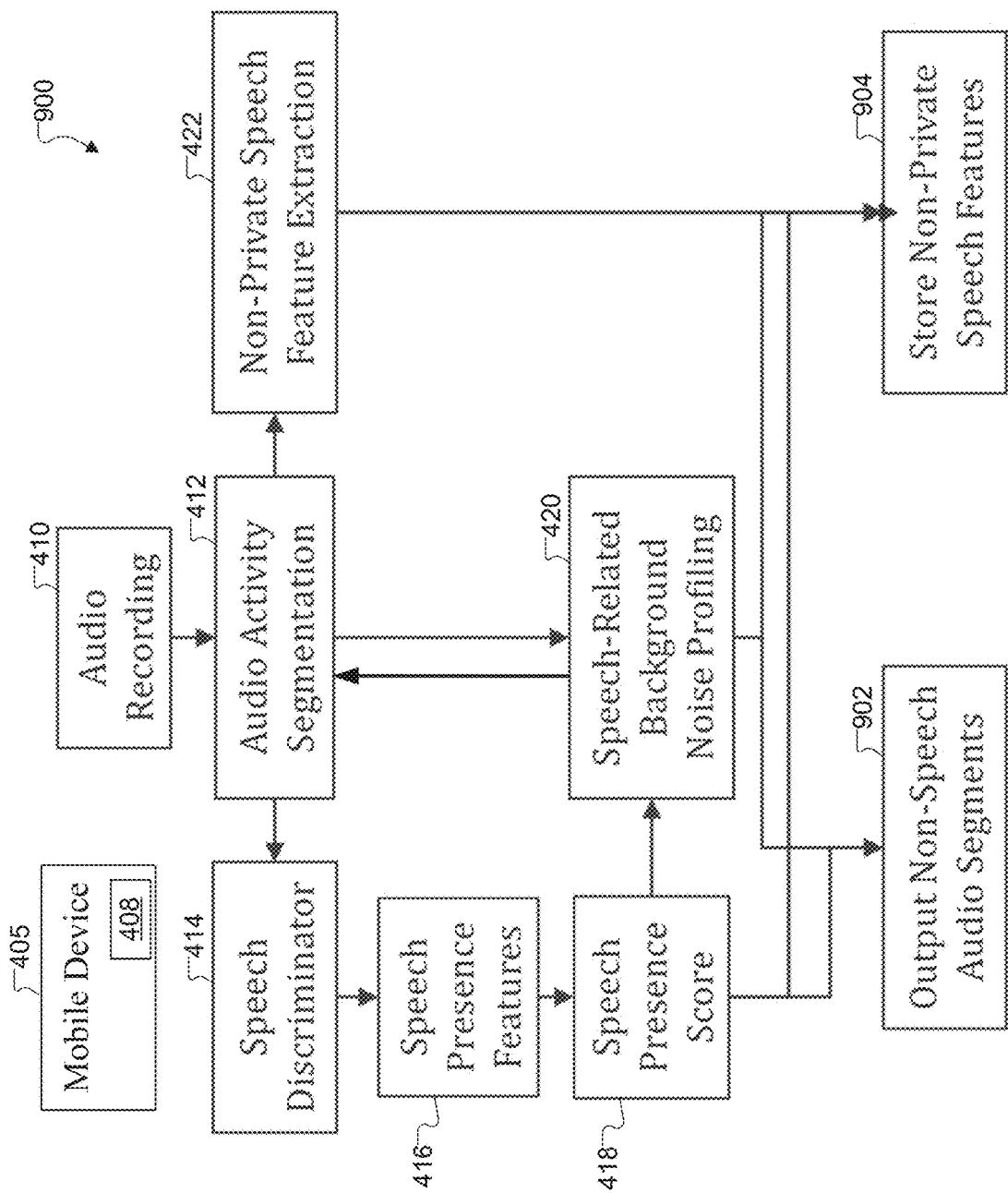
FIG. 9 illustrates still another example process for continuous, on-device, privacy-preserved collection of audio in accordance with this disclosure.

FIG. 9 illustrates still another example process 900 for continuous, on-device, privacy-preserved collection of audio in accordance with this disclosure. For ease of explanation, the process 900 is described as a variation of the process 400 shown in FIG. 4. However, the process 900 could involve any other suitable process and be used in any suitable system without departing from the scope of this disclosure.

As shown in FIG. 9, the process 900 includes a number of components and operations that are the same as or similar to corresponding components and operations of the process 400. For example, the mobile device 405 distinguishes and separates speech segments versus non-speech segments, the same as, or similar to, the process 400. However, in contrast to the process 400 (in which the mobile device 405 generates synthetic speech segments and obfuscated audio), the process 900 includes operations 902 and 904. In operation 902, the mobile device 405 outputs the non-speech segments. In operation 904, the mobile device 405 stores the non-private features of the speech segments. The non-private features of the speech segments can be sent to the cloud for further analysis of prediction or training.

Although FIG. 9 illustrates one example of a process 900 for continuous, on-device, privacy-preserved collection of audio, various changes may be made to FIG. 9. For example, various operations in FIG. 9 could overlap, occur in parallel, occur serially, occur in a different order, or occur any number of times.

Figure 10:
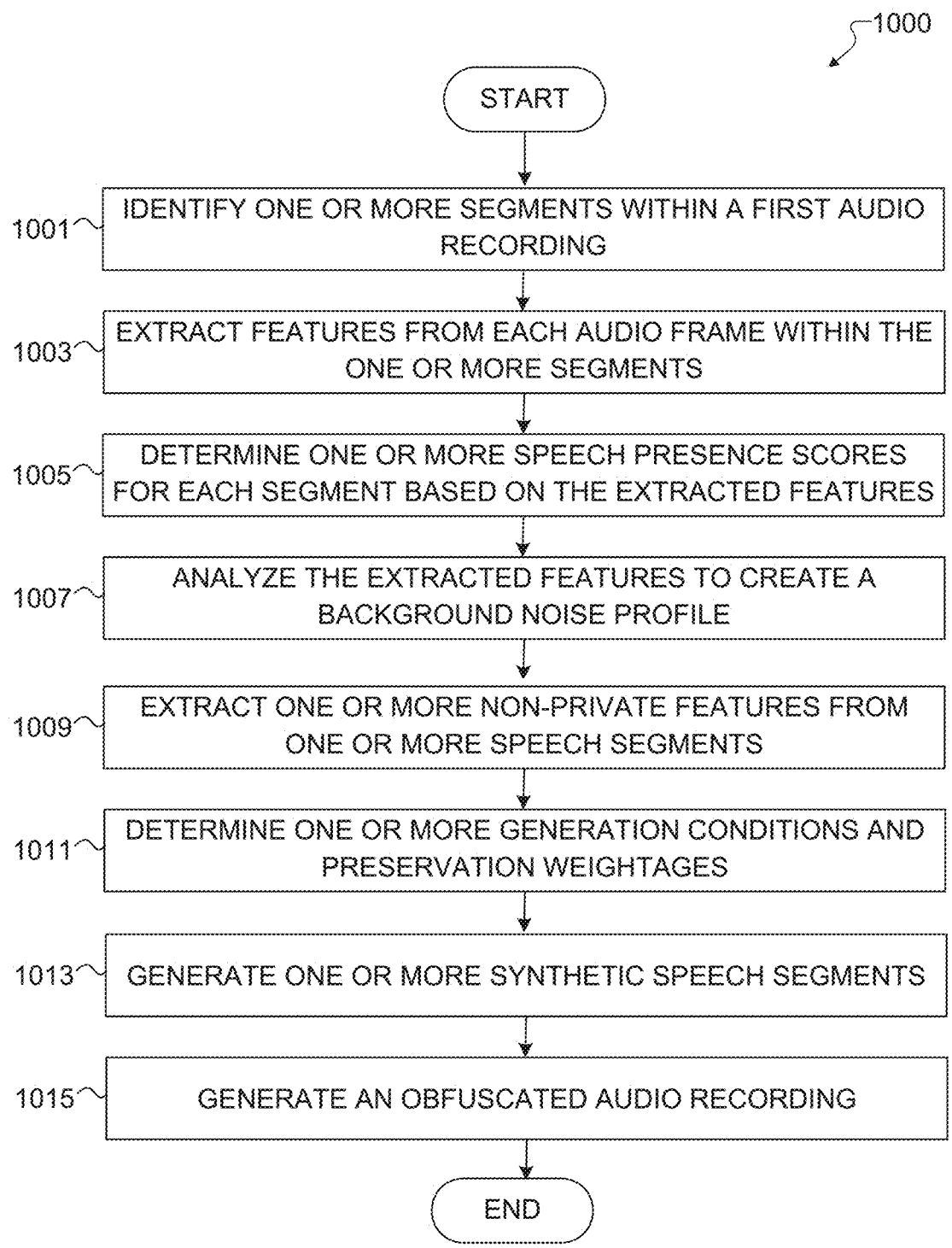
FIG. 10 illustrates an example method for continuous, on-device, privacy-preserved collection of audio in accordance with this disclosure.

FIG. 10 illustrates an example method 1000 for continuous, on-device, privacy-preserved collection of audio in accordance with this disclosure. For ease of explanation, the method 1000 shown in FIG. 10 is described as involving the process 400 shown in FIG. 4. However, the method 1000 could involve any other suitable process and be used in any suitable system without departing from the scope of this disclosure.

At operation 1001, one or more segments are identified within a first audio recording that includes one or more non-speech segments and one or more speech segments. This can include, for example, the mobile device 405 performing an audio recording function 410 to generate a raw audio recording and performing an audio activity segmentation function 412 to generate a list of audio activities.

At operation 1003, a plurality of features are extracted from each audio frame within the one or more segments based on a first machine learning model. The first machine learning model is trained to evaluate a similarity distance value between an audio frame and speech audio characteristics. This can include, for example, the mobile device 405 executing a speech discriminator module 414 to generate a set of speech presence features 416.

At operation 1005, one or more speech presence scores are determined for each segment based on the extracted features and a second machine learning model. The second machine learning model is trained to associate the extracted features with presence of only speech, only non-speech, or an overlap of speech and non-speech. This can include, for example, the mobile device 405 generating one or more speech presence scores 418 using a machine learning model f. In some embodiments, the one or more speech segments are identified based in part on the one or more speech presence scores.

At operation 1007, the extracted features are analyzed to create a background noise profile providing information of closeness of background noise of the first audio recording to one or more speech audio patterns. This can include, for example, the mobile device 405 generating a speech-related background noise profile 420. In some embodiments, the one or more speech segments are distinguished from the one or more non-speech segments based on the background noise profile.

At operation 1009, one or more non-private features are extracted from the one or more speech segments. The non-private features can include shimmer, jitter, or both. This can include, for example, the mobile device 405 performing a non-private speech feature extraction function 422 to extract non-private speech features from the speech segments.

At operation 1011, one or more generation conditions and preservation weightages are determined based on the non-private features by analyzing feature values and evaluating a priority of maintaining each feature based on prior knowledge. This can include, for example, the mobile device 405 determining one or more speech generation conditions 424 and one or more preservation weightages 426. In some embodiments, an objective of a learned generator module is adjusted based on the generation conditions. The learned generator module is trained for generation of one or more synthetic speech segments and the objective maintains the one or more non-private features.

At operation 1013, one or more synthetic speech segments are generated that include natural speech audio characteristics and that preserve one or more non-private features of the one or more speech segments. This can include, for example, the mobile device 405 executing the synthetic speech generation module 428 to generate synthetic speech segments 604 in accordance with the process 600. For example, the mobile device 405 can evaluate score values 606 for one or more entries in the synthetic speech segments 604 in comparison with corresponding speech segments based on the preservation weightage 426. The mobile device 405 can then select one or more synthetic speech segments 604 based on the score values 606.

At operation 1015, an obfuscated audio recording is generated by replacing the one or more speech segments with the one or more synthetic speech segments while maintaining the one or more non-speech segments. The one or more synthetic speech segments prevent recognition of some content of the obfuscated audio recording. This can include, for example, the mobile device 405 performing a feature-preserving speech obfuscation function 430 to generate an obfuscated audio recording 432. In some embodiments, the obfuscated audio recording can be sent to a second electronic device for use in audio analysis. For example, the mobile device 405 can send the obfuscated audio recording 432 to the cloud 434.

Although FIG. 10 illustrates one example of a method 1000 for continuous, on-device, privacy-preserved collection of audio, various changes can be made to FIG. 10. For example, various steps in FIG. 10 could overlap, occur in parallel, occur serially, occur in a different order, or occur any number of times. Also, the steps of the method 1000 could be implemented in any suitable manner, such as entirely within the mobile device 405 or using a combination of devices. For instance, as indicated above, the mobile device 405 could collect data and provide the data to a server 106, which could then process the data and generate any suitable output.

The embodiments disclosed herein can be used advantageously to maintain non-speech segments while obfuscating speech segments. During the speech obfuscation process, the private contents and identity of the subjects are removed and the non-speech speech features that may be needed for additional analysis (e.g., health assessments) are maintained. Users can carry their recording devices to different environments, and the disclosed embodiments can adapt to the condition and background noise to provide privacy-preserved audio monitoring and collection.

Applications for the disclosed embodiments can include various health assessments, including lung health assessment. However, possible applications are not limited to health assessments. The disclosed embodiments for privacy-preserved audio collection are applicable for any assessment that benefits from using non-speech audio activities within a recorded audio. Some examples include analyzing vocal cord dysfunction, cognitive impairment in subjects, or classification of environment sounds and locations.

The disclosed embodiments can also be integrated into voice assistants. For example, the disclosed speech presence score and background noise profiling can be used to improve detection of the "wake up" command, continuous detection of conversation, and privacy of audio collection with continuous listening capability.

Although this disclosure has been described with reference to various example embodiments, various changes and modifications may be suggested to one skilled in the art. It is intended that this disclosure encompass such changes and modifications as fall within the scope of the appended claims.

What is claimed is:

1. A method, comprising:
   identifying, by an electronic device, one or more segments within a first audio recording that includes one or more non-speech segments and one or more speech segments;
   extracting, by the electronic device, a plurality of features from each audio frame within the one or more segments based on a first machine learning model, wherein the first machine learning model is trained to evaluate a similarity distance value between an audio frame and speech audio characteristics;
   determining, by the electronic device, one or more speech presence scores for each segment based on the extracted features and a second machine learning model, wherein the second machine learning model is trained to associate the extracted features with presence of one of: only speech, only non-speech, or overlap of speech and non-speech;
   generating, by the electronic device, one or more synthetic speech segments that include natural speech audio characteristics and that preserve one or more non-private features of the one or more speech segments; and
   generating, by the electronic device, an obfuscated audio recording by replacing the one or more speech segments with the one or more synthetic speech segments while maintaining the one or more non-speech segments, wherein the one or more synthetic speech segments prevent recognition of some content of the obfuscated audio recording,
   wherein the one or more speech segments are identified based on the one or more speech presence scores.

2. The method of claim 1, further comprising:
   sending, by the electronic device, the obfuscated audio recording to a second electronic device for use in audio analysis.

3. The method of claim 1, further comprising:
   extracting the one or more non-private features from the one or more speech segments, wherein the one or more non-private features include at least one of: shimmer or jitter;
   determining generation conditions based on the one or more non-private features by analyzing feature values and evaluating a priority of maintaining each feature based on prior knowledge; and
   adjusting an objective of a third machine learning model based on the generation conditions, wherein the third machine learning model is trained for generation of the one or more synthetic speech segments and the objective maintains the one or more non-private features.

4. The method of claim 3, further comprising:
   determining a preservation weightage based on the one or more non-private features;
   evaluating score values for one or more entries in the one or more synthetic speech segments in comparison with corresponding one or more speech segments based on the preservation weightage; and
   selecting the one or more synthetic speech segments based on the score values.

5. The method of claim 1, further comprising:
   analyzing the extracted features to create a background noise profile providing information of closeness of background noise of the first audio recording to one or more speech audio patterns; and
   distinguishing the one or more speech segments from the one or more non-speech segments based on the background noise profile.

6. The method of claim 1, wherein the some content of the obfuscated audio recording that is prevented from being recognized comprises at least one of: speech content in the one or more speech segments, or identity information of a person that generated the speech content in the one or more speech segments.

7. The method of claim 1, wherein the first audio recording comprises sounds emanating from a user of the electronic device.

8. An electronic device comprising:
at least one audio sensor configured to generate a first audio recording; and
a processor configured to:
identify one or more segments within the first audio recording that includes one or more non-speech segments and one or more speech segments;
extract a plurality of features from each audio frame within the one or more segments based on a first machine learning model, wherein the first machine learning model is trained to evaluate a similarity distance value between an audio frame and speech audio characteristics;
determine one or more speech presence scores for each segment based on the extracted features and a second machine learning model, wherein the second machine learning model is trained to associate the extracted features with presence of one of: only speech, only non-speech, or overlap of speech and non-speech;
generate one or more synthetic speech segments that include natural speech audio characteristics and that preserve one or more non-private features of the one or more speech segments; and
generate an obfuscated audio recording by replacing the one or more speech segments with the one or more synthetic speech segments while maintaining the one or more non-speech segments, wherein the one or more synthetic speech segments prevent recognition of some content of the obfuscated audio recording,
wherein the one or more speech segments are identified based on the one or more speech presence scores.

9. The electronic device of claim 8, wherein the processor is further configured to:
control the electronic device to send the obfuscated audio recording to a second electronic device for use in audio analysis.

10. The electronic device of claim 8, wherein the processor is further configured to:
extract the one or more non-private features from the one or more speech segments, wherein the one or more non-private features include at least one of: shimmer or jitter;
determine generation conditions based on the one or more non-private features by analyzing feature values and evaluating a priority of maintaining each feature based on prior knowledge; and
adjust an objective of a third machine learning model based on the generation conditions, wherein the third machine learning model is trained for generation of the one or more synthetic speech segments and the objective maintains the one or more non-private features.

11. The electronic device of claim 10, wherein the processor is further configured to:
determine a preservation weightage based on the one or more non-private features;
evaluate score values for one or more entries in the one or more synthetic speech segments in comparison with corresponding one or more speech segments based on the preservation weightage; and
select the one or more synthetic speech segments based on the score values.

12. The electronic device of claim 8, wherein the processor is further configured to:
analyze the extracted features to create a background noise profile providing information of closeness of background noise of the first audio recording to one or more speech audio patterns; and
distinguish the one or more speech segments from the one or more non-speech segments based on the background noise profile.

13. The electronic device of claim 8, wherein the some content of the obfuscated audio recording that is prevented from being recognized comprises at least one of: speech content in the one or more speech segments, or identity information of a person that generated the speech content in the one or more speech segments.

14. The electronic device of claim 8, wherein the first audio recording comprises sounds emanating from a user of the electronic device.

15. A non-transitory computer readable medium containing computer readable program code that, when executed, causes at least one processor of an electronic device to:
identify one or more segments within a first audio recording that includes one or more non-speech segments and one or more speech segments;
extract a plurality of features from each audio frame within the one or more segments based on a first machine learning model, wherein the first machine learning model is trained to evaluate a similarity distance value between an audio frame and speech audio characteristics;
determine one or more speech presence scores for each segment based on the extracted features and a second machine learning model, wherein the second machine learning model is trained to associate the extracted features with presence of one of: only speech, only non-speech, or overlap of speech and non-speech;
generate one or more synthetic speech segments that include natural speech audio characteristics and that preserve one or more non-private features of the one or more speech segments; and
generate an obfuscated audio recording by replacing the one or more speech segments with the one or more synthetic speech segments while maintaining the one or more non-speech segments, wherein the one or more synthetic speech segments prevent recognition of some content of the obfuscated audio recording.

16. The non-transitory computer readable medium of claim 15, wherein the computer readable program code further causes the at least one processor to:
control the electronic device to send the obfuscated audio recording to a second electronic device for use in audio analysis.

17. The non-transitory computer readable medium of claim 15, wherein the computer readable program code further causes the at least one processor to:
extract the one or more non-private features from the one or more speech segments, wherein the one or more non-private features include at least one of: shimmer or jitter;

determine generation conditions based on the one or more non-private features by analyzing feature values and evaluating a priority of maintaining each feature based on prior knowledge; and adjust an objective of a third machine learning model based on the generation conditions, wherein the third machine learning model is trained for generation of the one or more synthetic speech segments and the objective maintains the one or more non-private features.

18. The non-transitory computer readable medium of claim 17, wherein the computer readable program code further causes the at least one processor to:

determine a preservation weightage based on the one or more non-private features;

evaluate score values for one or more entries in the one or more synthetic speech segments in comparison with corresponding one or more speech segments based on the preservation weightage; and select the one or more synthetic speech segments based on the score values.

19. The non-transitory computer readable medium of claim 15, wherein the computer readable program code further causes the at least one processor to:

analyze the extracted features to create a background noise profile providing information of closeness of background noise of the first audio recording to one or more speech audio patterns; and distinguish the one or more speech segments from the one or more non-speech segments based on the background noise profile.

20. The non-transitory computer readable medium of claim 15, wherein the first audio recording comprises sounds emanating from a user of the electronic device.

* * * * *